US012594385B2

(12) United States Patent
Ghershony

(10) Patent No.: US 12,594,385 B2
(45) Date of Patent: Apr. 7, 2026

(54) MEDICAL VAPORIZER WITH PRECISION CONTROLLED VAPOR COMPOSITION

(71) Applicant: Arie Ghershony, Bethesda, MD (US)

(72) Inventor: Arie Ghershony, Bethesda, MD (US)

( * ) Notice: Subject to any disclaimer, the term of this patent is extended or adjusted under 35 U.S.C. 154(b) by 584 days.

(21) Appl. No.: 18/125,110

(22) Filed: Mar. 22, 2023

(65) Prior Publication Data

US 2023/0330360 A1      Oct. 19, 2023

Related U.S. Application Data

(60) Provisional application No. 63/322,959, filed on Mar. 23, 2022.

(51) Int. Cl.
A61M 15/00      (2006.01)
A61M 11/04      (2006.01)

(52) U.S. Cl.
CPC ...... A61M 15/0003 (2014.02); A61M 11/041 (2013.01); A61M 15/002 (2014.02); A61M 15/0021 (2014.02); A61M 2205/123 (2013.01); A61M 2205/3331 (2013.01); A61M 2205/3368 (2013.01); A61M 2205/502 (2013.01)

(58) Field of Classification Search
CPC ...... A61M 11/04; A61M 15/06; A61M 15/00; A61M 11/041; A61M 15/008; A61M 15/0081; A61M 15/0066; A61M 15/0003; A61M 15/002; A61M 15/0021; A61M 2205/123; A61M 2205/3331; A61M 2205/3368; A61M 2205/502; A61M 11/02; A24F 40/30; A24F 40/485; A24F 40/50; A24F 40/60; A24F 40/65; A24F 40/10; A24F 40/57; G16H 20/13
See application file for complete search history.

(56) References Cited

FOREIGN PATENT DOCUMENTS

WO      WO-2020186361 A1 *   9/2020   ............. A24F 40/46

* cited by examiner

*Primary Examiner* — Ophelia A Hawthorne
(74) *Attorney, Agent, or Firm* — Larisa Migachyov

(57)      ABSTRACT

A medical vaporizer is provided, comprising a temperature-controlled heating module that provides a high level of control over vapor composition. The vaporizer also comprises a mouthpiece that produces a helical vortex of vapor at the outlet.

20 Claims, 14 Drawing Sheets

SECTION A-A

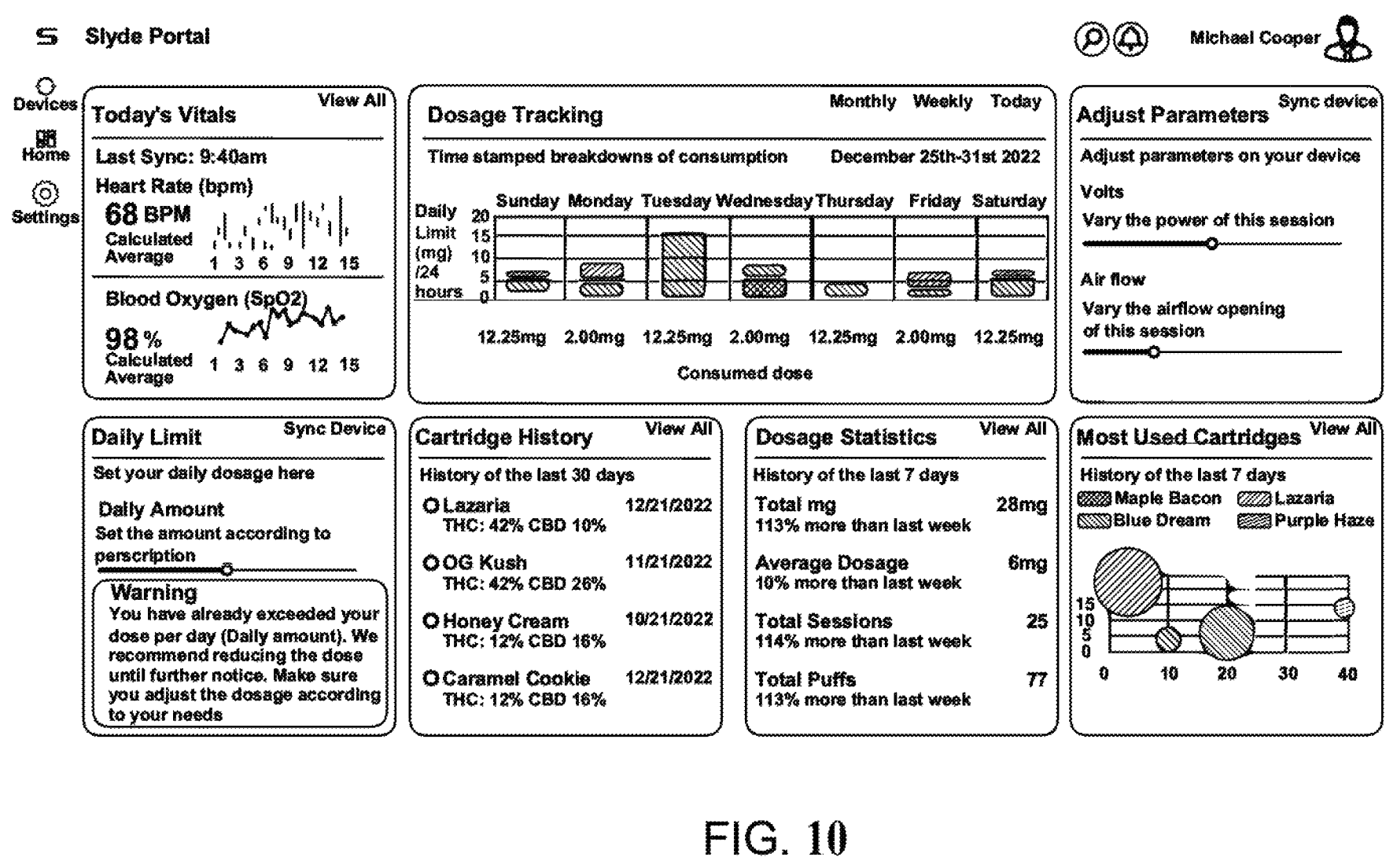

Michael Cooper

S   Slyde Portal

Devices

Home

Settings

Today's Vitals     View All

Last Sync: 9:40am

Heart Rate (bpm)

68 BPM

Calculated Average    1   3   6   9   12   15

Blood Oxygen (SpO2)

98 %

Calculated Average    1   3   6   9   12   15

Daily Limit     Sync Device

Set your daily dosage here

Daily Amount

Set the amount according to perscription

Warning

You have already exceeded your dose per day (Daily amount). We recommend reducing the dose until further notice. Make sure you adjust the dosage according to your needs

Dosage Tracking     Monthly   Weekly   Today

Time stamped breakdowns of consumption     December 25th-31st 2022

Daily Limit (mg) /24

20
15
10
5
0

Sunday   Monday   Tuesday   Wednesday   Thursday   Friday   Saturday hours 12.25mg   2.00mg   12.25mg   2.00mg   12.25mg   2.00mg   12.25mg Consumed dose

Cartridge History     View All

History of the last 30 days

○ Lazaria    12/21/2022
THC: 42% CBD 10%

○ OG Kush    11/21/2022
THC: 42% CBD 26%

○ Honey Cream    10/21/2022
THC: 12% CBD 16%

○ Caramel Cookie    12/21/2022
THC: 12% CBD 16%

Adjust Parameters     Sync device

Adjust parameters on your device

Volts

Vary the power of this session

Air flow

Vary the airflow opening of this session

Most Used Cartridges     View All

History of the last 7 days

▨ Maple Bacon   ▨ Lazaria
▨ Blue Dream   ▨ Purple Haze 15
10
5
0

0    10    20    30    40

Dosage Statistics     View All

History of the last 7 days

Total mg    28mg
113% more than last week

Average Dosage    6mg
10% more than last week

Total Sessions    25
114% more than last week

Total Puffs    77
113% more than last week

FIG. 10

MEDICAL VAPORIZER WITH PRECISION CONTROLLED VAPOR COMPOSITION

CROSS-REFERENCE TO RELATED APPLICATIONS

The present application takes priority from Provisional App. No. 63/322,959, filed Mar. 23, 2022, which is incorporated herein by reference.

BACKGROUND

Field of the Invention

The present invention relates generally to medical inhalers, and more specifically to inhalers and vaporizers that enable a user to precisely control vapor composition.

Background

Consumers utilize electronic vapor cigarettes, pipes, and modified vapor devices to enjoy what is commonly known as "vaping." Electronic vapor devices are characterized by vaporizing a medium to be inhaled. Vaporizable media (e.g., fluid) can be supplied by one or more replaceable cartridges. However, there are many unknowns since the cartridge is analogous to the proverbial black box. There is no way to know the contents of the cartridge. There is no way to measure what is left in the cartridges. And there is no real time feedback of the effect of the vaporizable media on users. These 'unknowns' or uncertainties are an albatross around the neck of the electronic vapor device industry, preventing further acceptance and use of this otherwise safe and enjoyable hobby for recreational users or a medicinal delivery system that allow medicinal cannabinoid formulation to be absorbed directly into the blood stream.

Currently, accurate dosing of medical cannabis compounds (THC, CBD etc.) is only possible via oral administration in either oil or pill form. Since THC has a different effect and application from CBD, it is important to control the proportions of these compounds to treat various medical conditions. While it is possible to do so via oral administration, some users prefer to inhale their cannabis compounds, since the effect is produced immediately (as opposed to 45-90 minutes for oral administration) and the acute effects last only for 2-5 hours, as opposed to 6 or more hours for oral administration.

Currently available vaporizers used for cannabis do not have an accurate enough control over the temperature at which the cannabis is vaporized, or the exact composition of the vaporizable material in the cartridge. Cannabis contains many therapeutically active compounds, such as THC, CBD, and more than 150 types of terpenes. Each of those compounds has a different boiling point. If the temperature of vaporization is set too high, some of the terpenes may burn, affecting vapor composition and therapeutic effect. Vaping at a lower temperature will give the user more terpenes; vaping at a higher temperature will give the user more vapor and a more intense effect. Furthermore, the THC to CBD ratio may also be affected by temperature. The prior art does not currently allow a way to dynamically adjust vapor composition during a vaping session in order to exercise a precise control over its effect.

Furthermore, currently available vaporizers often do not provide the user with enough transparency over exactly what the vaporizer is doing. While some of the prior art is connected to apps, most users do not download them-only 25% of all users download such apps, and only 5-10% of them use them.

Moreover, currently available vaporizers do not provide the user with any feedback over what the vapor is doing in their body. A medical cannabis user may want to monitor their heart rate, blood pressure, or other medical parameters, and have the composition of the cannabis they are consuming depend on those medical parameters.

A need exists for a vaporizer that enables a user to have a more precise control over vapor composition, more transparency into exactly what they are consuming, and feedback over what the vapor is doing in their body.

LIST OF FIGURES

FIG. 10 shows a screenshot from a dashboard for a computer interface with an embodiment of the present invention.

SUMMARY OF THE INVENTION

Figure 1:
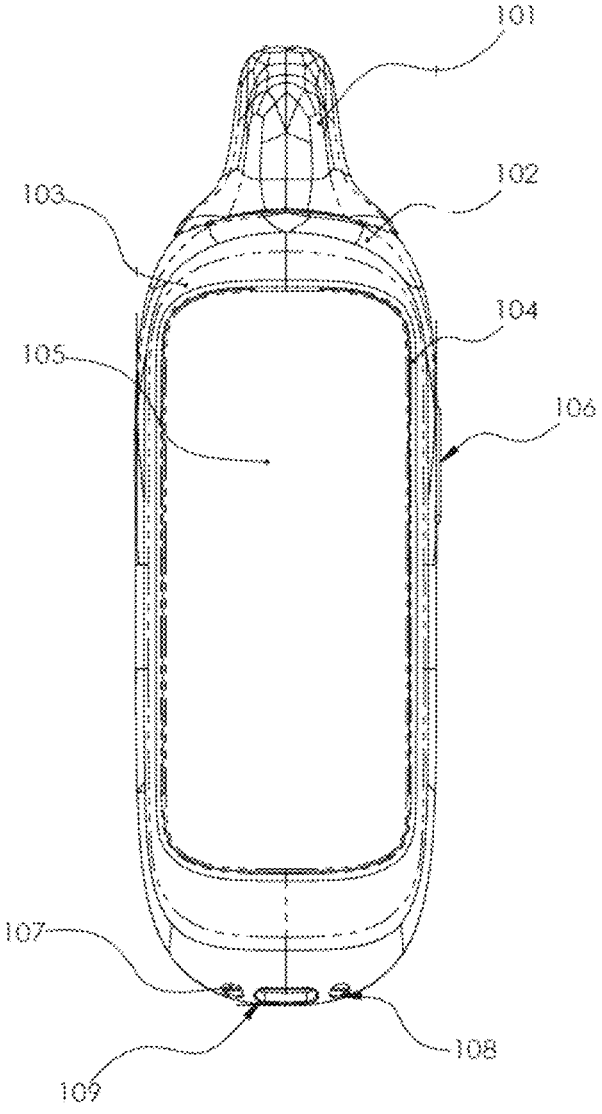
FIG. 1 shows a front view of an embodiment of the present invention.

An object of the present invention is to provide a vaporizer that adjusts heating temperature of a liquid substance in order to produce vapor of varying compositions.

Another object of the present invention is to provide a vaporizer that enables a user to select a precise dosage of each active compound or a precise proportion of different vaporizable materials without the need for an external app.

Another object of the present invention is to provide a vaporizer with an efficient cooling system for the vapor that controls the temperature in a precise way.

Another object of the present invention is to provide a vaporizer that receives data from wearable devices and adjusts vapor dosages depending on this data.

Another object of the present invention is to provide a vaporizer with a mouthpiece assembly that provides an efficient air flow for terpene-containing vapor without sacrificing flavor.

In an aspect of the present invention, a vaporizer is provided, comprising a cartridge with a liquid substance to be vaporized. The liquid substance comprises at least two vaporizable compounds with different boiling points. The vaporizer also comprises a heating unit that heats the cartridge to vaporize the liquid substance. In an aspect of the present invention, the heating unit heats the liquid substance to at least two different temperatures to result in at least two different vapor compositions that are then delivered to a user via a mouthpiece, wherein the percentage of at least one of the vaporizable compounds is different between the two different vapor compositions. The temperature change can be abrupt or gradual over a particular period of time.

In an aspect of the present invention, the vaporizer comprises a second cartridge containing a second liquid substance, and a second heating unit, wherein each cartridge and each heating unit are controlled independently to result in varying vapor compositions. The vapor coming from each cartridge is then mixed together to create a mixture. The temperature of at least one of the heating units is then changed to change the composition of the mixture.

In an aspect of the present invention, the liquid substance comprises a third compound, wherein the boiling point of the third compound is different from the boiling points of the first and second compound.

In an aspect of the present invention, the vaporizer communicates wirelessly with a wearable device that measures a particular physiological parameter. The vaporizer then can change vapor composition or stop vapor delivery altogether when the physiological parameter reaches a certain predetermined value.

In an aspect of the present invention, the vaporizer is calibrated to determine a correlation between a temperature of the heating unit and vapor composition; this can be performed by gas chromatography or mass spectrometry. The correlation may then be stored in memory.

In an aspect of the present invention, before delivering a vapor to the user, it is mixed with a predetermined amount of ambient air to obtain a gas mixture at approximately 30° C. The mixing step may involve calibrating the vaporizer by either measuring a user's inhalation volume or calculating a user's inhalation volume from the user's biometric parameters. The mixing step may also include calculating a flow rate for ambient air and a flow rate for the first vapor to obtain a gas mixture at approximately 30° C., and controlling the flow rate for each to maintain the gas mixture at the correct temperature.

In an aspect of the present invention, the vapor is mixed with ambient air by directing it along a helical path through the mouthpiece of the device to create a vortex.

In an aspect of the present invention, at least one of the temperatures is a boiling point of a compound. Since vapor pressure inside the cartridge may be different from atmospheric air pressure, a pressure sensor may be present to measure the vapor pressure of the liquid pressure and to adjust the temperature accordingly so that the boiling point of the desired compound is maintained.

In an aspect of the invention, at least one of the cartridges is a standard 510 cartridge.

In an aspect of the invention, a touchscreen is provided to enable a user to interact with the vaporizer.

DETAILED DESCRIPTION

The following detailed description is of the best currently contemplated modes of carrying out exemplary embodiments of the invention. The description is not to be taken in a limiting sense, but is made merely for the purpose of illustrating the general principles of the present invention.

It is to be understood that the present invention may be used with any vaporizable liquid substance. While the below embodiment discloses the use of the present invention with cannabis, the present invention is not limited to cannabis. Any vaporizable liquid substance that comprises multiple compounds that have different boiling points is usable with the present invention. The below disclosure describes the use of the present invention with cannabis only as an illustration.

A significant advantage of the present invention is that it enables a user to dynamically adjust vapor composition using the same liquid substance in the same cartridge during a use session. Cannabis contains many active compounds and they have different boiling points. A non-exhaustive list of some representative sample cannabinoids and their boiling points is presented below:

| Cannabinoid | Boiling point |
|---|---|
| CBG | 126° F. |
| THCa | 220° F. |
| CBDa | 248° F. |
| Δ9THC | 315° F. |
| Δ8THC | 350° F. |
| CBD | 356° F. |
| CBN | 365° F. |
| THC | 428° F. |
| CBC | 428° F. |

Cannabis also contains varying terpenes, which also have therapeutic and psychoactive effects. A non-exclusive list of the terpenes contained in cannabis and their boiling points is summarized below:

| Terpene | Boiling Point |
|---|---|
| α-Pinene | 311° F. |
| β-Caryophyllene | 320° F. |
| β-Myrcene | 334° F. |
| Citronellol | 437° F. |
| d-Limonene | 349° F. |
| Eucalyptol | 349° F. |
| Terpinolene | 365° F. |
| Linalool | 388° F. |
| Humulene | 388° F. |
| Phytol | 399° F. |
| Caryophyllene Oxide | 495° F. |

As can be seen from the above tables, there are many different compounds present in cannabis and they have radically different boiling temperatures. Thus, heating the same cannabis-containing liquid substance to different temperatures, or to a particular variation of temperatures, will result in radically different vapor compositions from the same substance.

Furthermore, some compounds, such as cannabinoids, can withstand a higher temperature than their boiling points. However, terpenes, which are plant oils that give cannabis its taste and smell, cannot withstand higher temperatures. Thus, vaping at a lower temperature will produce a vapor with more terpenes and a more perfume-like flavor, while vaping at a higher temperature will produce a vapor with more THC and CBD and fewer terpenes. The temperature may be adjusted during a vaping session to dynamically alter vapor composition.

In an embodiment, the present invention may be a dual (or multiple) cartridge system. This enables the user to be even more flexible about dynamically adjusting vapor composition. For example, each cartridge could comprise a different extract formulation with different percentages of active compounds such as THC and CBD. Each cartridge preferably has its own heating element that can be set to a specific temperature that produces the desired ratio of active compounds. Mixing the vapor from each cartridge allows the user to dynamically adjust vapor composition in a very flexible way during a use session.

The most commonly used cannabinoids, CBD and Δ9THC (which is commonly referred to as simply THC), have very different effects on the human body and brain. THC is a psychoactive constituent of cannabis that attaches itself to endocannabinoid receptors in the brain, located in the cerebral cortex, cerebellum, and basal ganglia; these are the parts of the brain responsible for thinking, memory, pleasure, coordination, and movement. It can be used for treating spasticity and chronic pain in various neurological diseases, such as multiple sclerosis. CBD is devoid of psychoactive activity, and has multiple analgesic, anti-inflammatory, antineoplastic, and chemopreventive activities. It can be used to inhibit cancer cell invasiveness and metastasis as well as treating seizures associated with many different conditions. Since these two compounds are different in their effects and purposes, many medicinal cannabis formulations have a precise ratio of THC to CBD, and it is very important to maintain such a precise ratio in vapor as well.

Some patients may require a different ratio of THC to CBD at different times of day or night, or in different situations depending on symptoms. For example, a patient may want more THC at night when they are about to go to sleep, and more CBD during the day when they simply want to relieve pain without any psychoactive effects.

Some patients may require a varying ratio of THC to CBD as their use session progresses; for example, a patient may want more CBD at the start of the session and then more THC at the end.

Terpenes also have an effect on the human body and brain and have a synergistic effect with THC, CBD, or both. For example, a-pinene inhibits the activity of acetylcholinesterase in the brain; therefore, it can aid memory and minimize cognitive dysfunction induced by THC intoxication. Further, it possesses antiseptic activity. β-myrcene increases the analgesic effects of THC and CBD by stimulating the release of endogenous opioids, as well as being an antioxidant and anticarcinogen. Limonene can boost the level of serotonin and dopamine, thereby inducing the anxiolytic, anti-stress, and sedative effects of the CBD. Caryophyllene is responsible for cannabis anti-inflammatory effects and provides gastroprotective, analgesic, anticancerogenic, antifungal, antibacterial, and neuroprotective effects. Many other terpenes have other varying effects on the human body and mind. It is to be understood that the above disclosure is not a limitation on the types of terpenes, or the types of substances in general, that could be covered by the present invention.

Overview of the Device

In an aspect of the present invention, a vaporizer is provided. The vaporizer may be used for administering different compounds through inhalation. While the present disclosure focuses on cannabis uses, it is not meant to be limited to cannabis. It may be used to administer nicotine or any other compounds that can be inhaled. The liquid or liquids to be vaporized is contained in cartridges. In an aspect of the invention, the cartridges are standard cartridges with 510 threading, though this is not required to practice the present invention.

One of the advantages of the present invention is that it enables a user to dynamically adjust the exact composition of the inhaled vapor during a use session or between different use sessions without swapping out cartridges. In the preferred embodiment of the present invention, this is done by a touchscreen that enables a user to precisely control vapor composition during a use session or to set a predetermined program before a use session.

The present invention preferably connects directly to the cloud without requiring the intermediation of a mobile application. In an embodiment, this connection is established through the Internet of Things (IoT) protocol, which enables the device to consume and send data to a cloud server in real time. Thanks to this cloud connection, the device can be monitored and managed remotely. For example, the device could be monitored and managed by a medical provider. Also, the cloud connection enables the device to receive updates and enhancements seamlessly.

Figure 2:
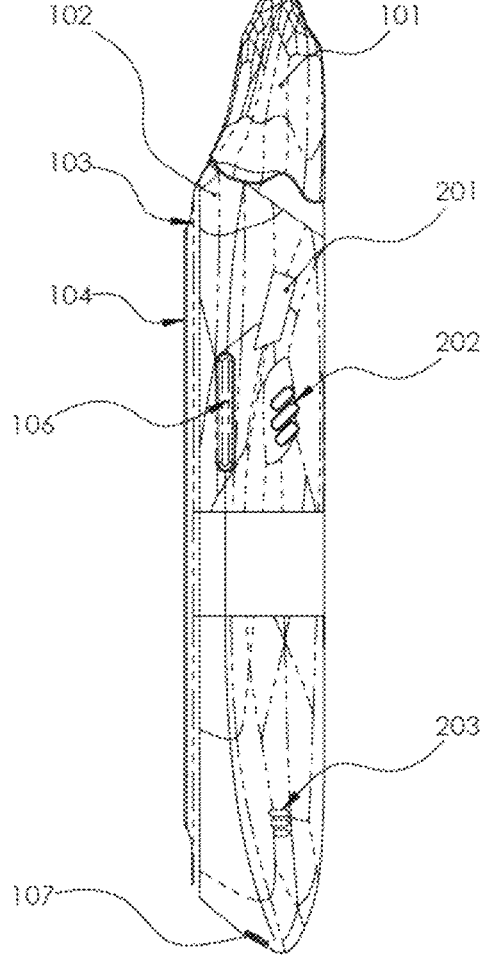
FIG. 2 shows a side view of an embodiment of the present invention.
Figure 3:
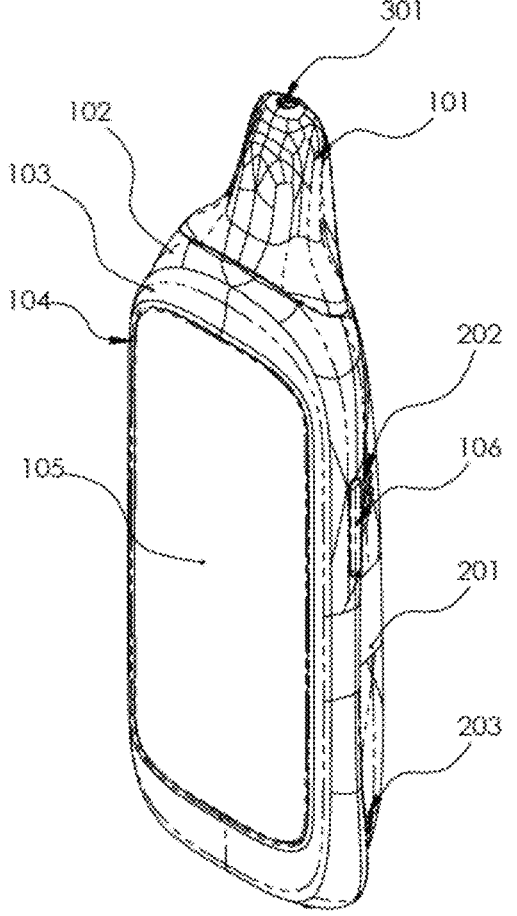
FIG. 3 shows an isometric view of an embodiment of the present invention.

FIGS. 1, 2, and 3 show three views of an embodiment of the present invention. This embodiment of the vaporizer 100 of the present invention comprises a mouthpiece 101 through which vapor can be inhaled, a housing 102 and 103 containing the internal components of the vaporizer, a large touchscreen 105 surrounded by a touchscreen bumper 104, an interaction button 106, a charger port 109, and two pogo pin holes 107 and 108 for the charger station. The side view shown in FIG. 2 shows the back side of the housing 201, the side air intake holes 202 for the flow control system of the present invention, and side holes 203 for sound propagation. The isometric view shown in FIG. 3 also shows the mouthpiece outlet 301.

Figure 4:
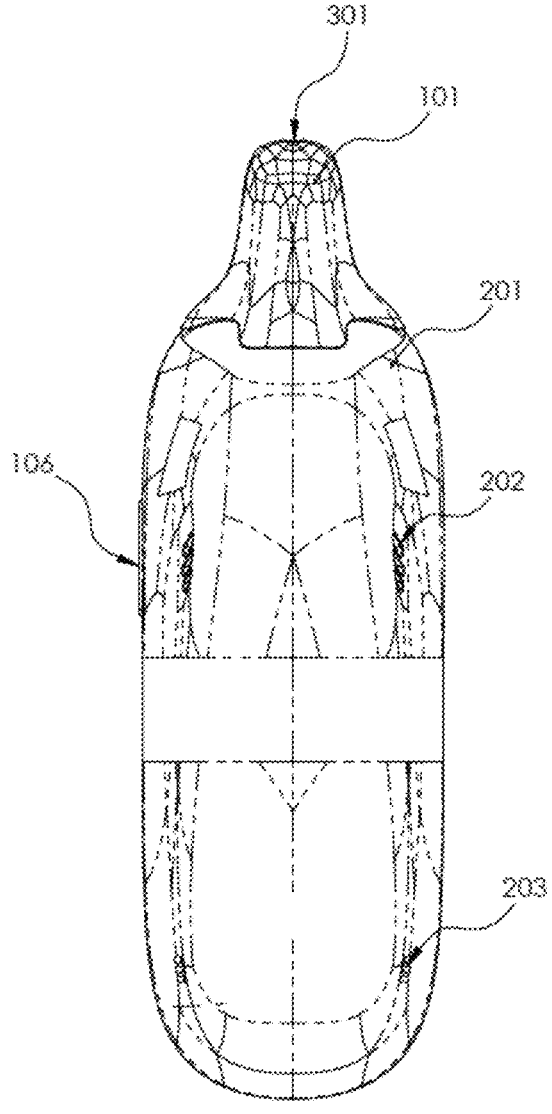
FIG. 4 shows a back view of an embodiment of the present invention.
Figure 6:
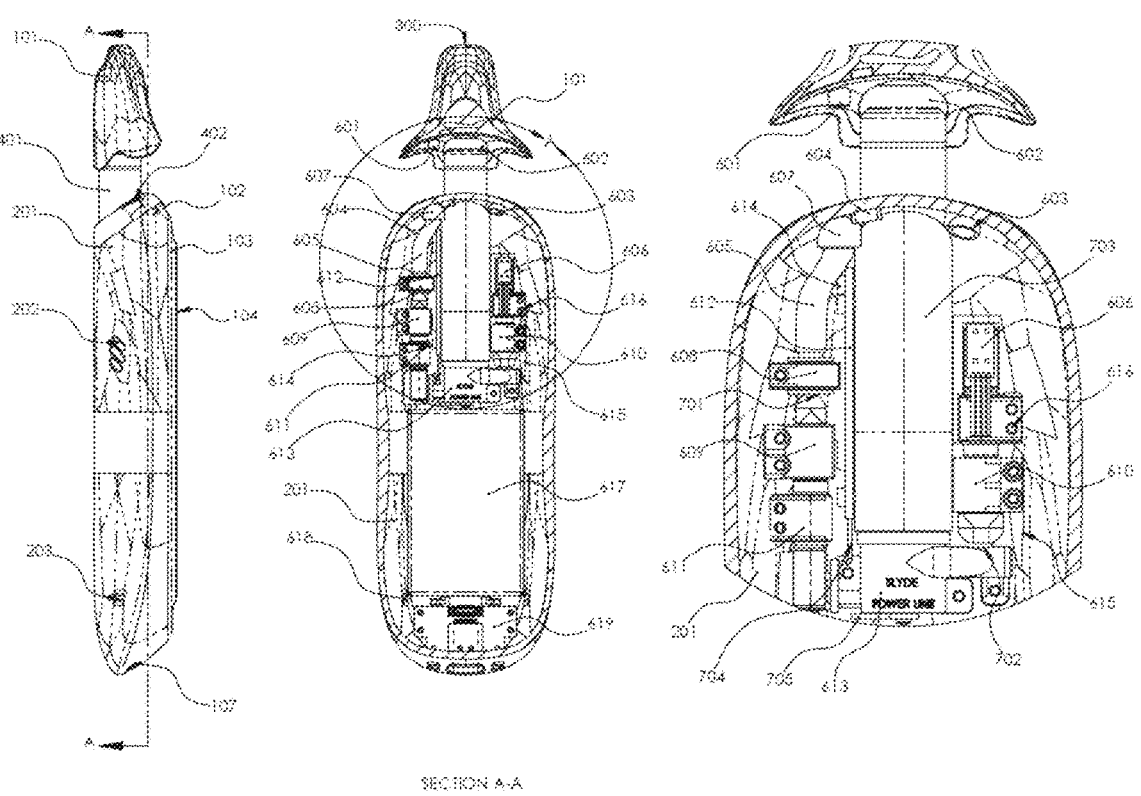
FIG. 6 shows a cross-sectional view and a magnified view of an embodiment of the present invention.

FIG. 4 shows the back view of an embodiment of the present invention. FIG. 6 shows a cross-sectional view of an embodiment of the present invention, with a magnified detail view as well, showing the mouthpiece 101 removed and a dual cartridge 401 visible. A rubber female fitting 402 for the ambient air conduit is shown as displayed. The front section view shows the male fitting 601 for the ambient air conduit, which connects to the female fitting 402 when the mouthpiece 101 is fully attached to the vaporizer. The ambient air conduit provides airflow of ambient air to the mouthpiece to mix with the vapor, as will be discussed below. The ambient air flows through ambient air conduit tubing 605 which connects to a round slot 607 to connect the tubing to the mouthpiece. A ambient air conduit valve seat bracket 608 is used to hold the air flow control valve 611 in place. Both vapor flow and secondary conduit airflow are controlled by endless screws; this enables very precise control. Main stepper rail bracket 610 and secondary stepper rail bracket 609 are used to hold the valves in place to prevent unwanted rotation. The vapor flow control valve is placed in a vapor flow control valve seat 702 and the air flow control valve is placed in an air flow control valve seat 701. The valves are connected with wires 704. The cartridges are connected to power unit terminals 705.

The two cartridges 401 fit into a cartridge slot 602 in the mouthpiece and cartridge slot 703 in the housing. Magnets 603 and 604 are used to attach the mouthpiece to the vaporizer when it is in use.

This embodiment shows a dual cartridge 401, comprising two cartridges connected together axially-a first cartridge and a second cartridge. More detail on the structure of the dual cartridge will be discussed below. Second cartridge power board 612 drives power to a second cartridge and extracts data from both cartridges. The second cartridge power board 612 also comprises connectors to the air flow control valve 612.

Three omniball pogo pins 614 are used to connect the second cartridge to the vaporizer; two of the pogo pins are used for data transmission, and the third is used as a positive power pin for the secondary cartridge.

Air intake filters 615 are mounted on the housing for the air flow system. Screw holes 616 are used to attach the parts of the housing together. Side holes 203 preferably also comprise filters 618.

The device is preferably powered by a lithium battery 617, preferably a 1500 mA LiPo battery with a high discharge current capacity.

The device preferably comprises at least one processor and memory that is sufficient to provide control signals for the present invention. In an embodiment of the invention, the device comprises two 240 MHz microprocessors that are constantly communicating with each other to maintain the balance of system operations. A first MCU manages Wi-Fi communication, Flash, and SD dies, and communicates with the embedded GPU that runs at 70 MHz through an 18-bit RGB interface. The second MCU manages all the operations related to inhalation, including data collection from the bank of sensors and control of the PID system.

Figure 5:
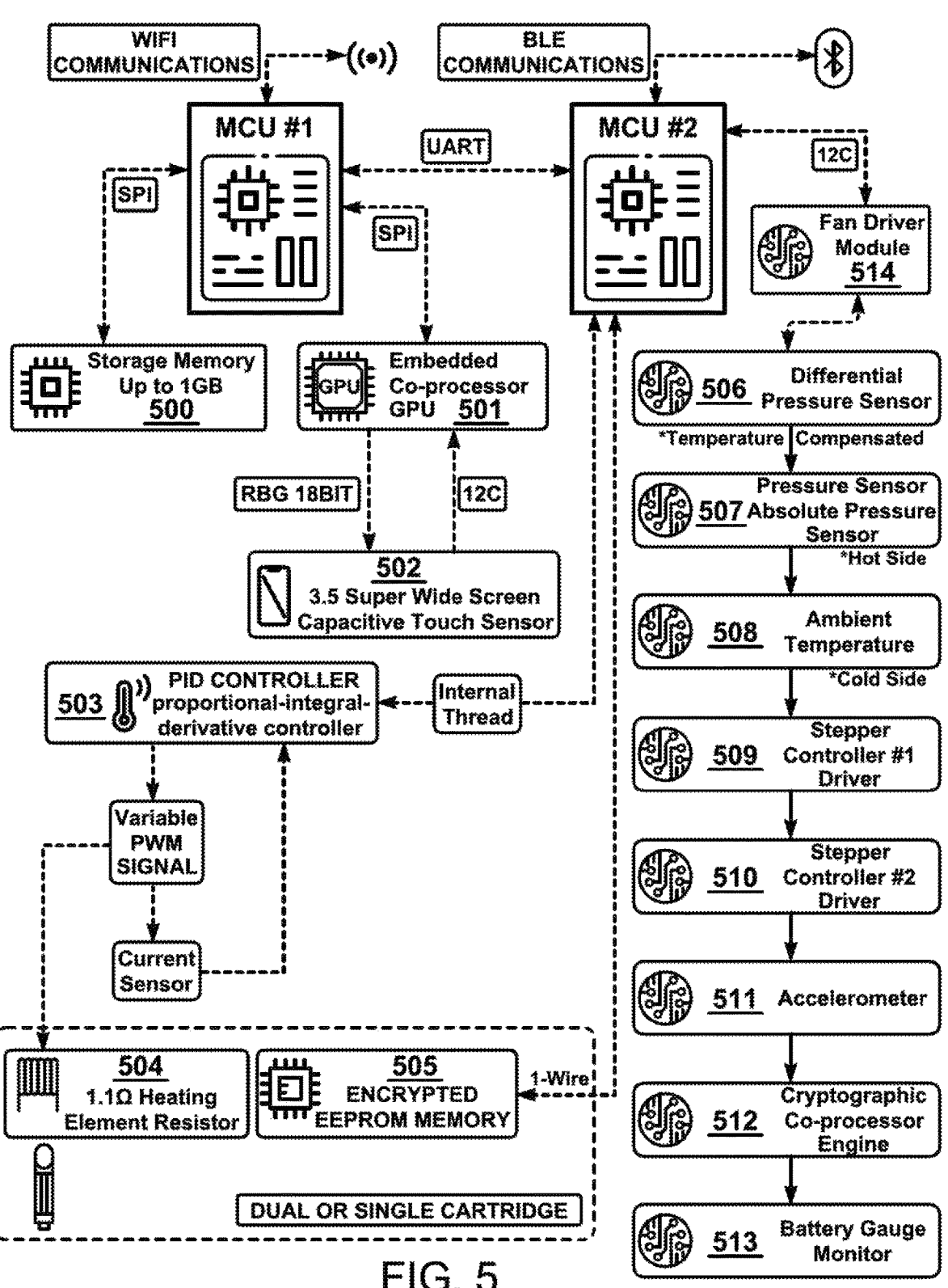
FIG. 5 shows a diagram of the hardware of an embodiment of the present invention.

FIG. 5 shows a diagram of the hardware of an embodiment of the present invention. As mentioned above, the device comprises two 240 MHz microprocessors, MCU #1 and MCU #2. MCU #1 is connected to a storage memory 500 for storing data and programs. It is also connected to wi-fi via a communication module, and connected to an embedded co-processor GPU 501. The embedded co-processor GPU 501 controls the touchscreen, which, in this embodiment, is a 3.5" super wide screen capacitive touch sensor 502. MCU #1 also communicates with the other microprocessor, MCU #2, which is the microprocessor responsible for controlling the vaporizer functions of the vaporizer. It is connected to a PID controller 503 for controlling the temperature of the heating unit 504 in the cartridge. The PID controller 503 delivers a variable PWM signal to the heating unit 504 to ensure that the correct temperature is maintained. The cartridge also comprises an encrypted EEPROM memory 505, which is also connected to the MCU #2. The MCU #2 is also responsible for receiving data from the sensors incorporated in the device. In an aspect of the invention, the sensors include a differential pressure sensor 506 (for temperature compensation), an absolute pressure sensor 507, an ambient temperature sensor 508, and an accelerometer 511. The MCU #2 also controls the stepper controllers 509 and 510 for controlling the flow of ambient air and vapor through the cartridge. Finally, the MCU #2 also is connected to the cryptographic co-processor engine and a battery gauge monitor. The cryptographic co-processor engine is used to encrypt the data stored on the device, since privacy and security of user data is of utmost importance in medical applications where a user's data is highly private. Since the device can store data locally, with strong encryption mechanisms, this ensures that user data is protected even in the absence of an Internet connection. In an embodiment, RSA encryption and secure https connections are used for communications with the cloud, and AES256 encryption of data is used for data stored within the device. In an embodiment, the unique key for each device is only known by the cloud server, not the device itself. This ensures that even if a device is lost or stolen, the data stored within it cannot be accessed. The cryptographic coprocessor within the device is responsible for storing all encryption keys and ensures that the device operates as a hardware accelerator, with secure hardware-based key storage. This is useful for patient privacy as well as for medical studies, since this feature ensures that medical data is protected against unauthorized access and tampering.

The first and second MCUs preferably communicate via a customized communications protocol that utilizes the Serial Peripheral Interface (SPI) of the two microcontrollers. This allows for quick actions in response to user feedback, and ensures the safety and reliability of the device.

It is to be understood that while the above described embodiment comprises two microprocessors, the present invention incorporates any number of microprocessors, as long as it is sufficient to carry out the functions of the present invention.

The device preferably comprises a communication module connected to the processors. The communication module may use Wi-Fi, Bluetooth, or any other wireless communication protocol. The communication module may be used to connect the device to a wearable, such as a Fitbit or an Apple Watch, or to connect to a computing device such as a server or a computer.

In short, the vaporizer disclosed in the preferred embodiment of the present invention comprises a dual cartridge, each cartridge preferably containing a liquid of different composition. Triple cartridges, or assemblies of more than three cartridges, are also included in the present invention, as is an embodiment comprising a single cartridge. In an embodiment, standard 510 cartridges are used for the present invention, to enable greater standardization and to enable a user to have a broader range of available options for liquids to be vaporized. Each cartridge is individually controlled by a PID heating module, allowing for real-time regulation of temperature, power, and delivered dose for each cartridge, and thus for the vapor delivered to the user.

The vaporizer also comprises a large touchscreen that comprises a user-friendly graphical interface. The touchscreen preferably enables a user to set and adjust vapor composition, and to view usage statistics directly on the device, as will be described below.

Figure 7:
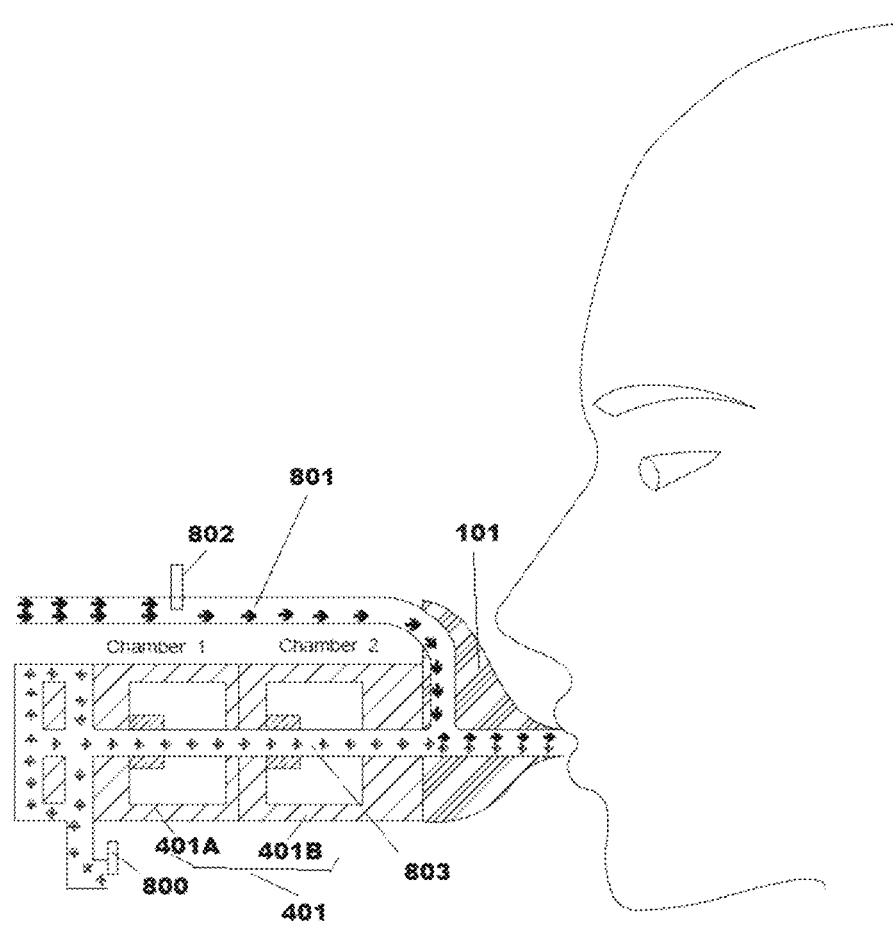
FIG. 7 shows a high-level diagram of the airflow through the present invention.

Furthermore, the vaporizer also comprises a cooling system and airflow regulation system that enables the vapor to be highly controlled for temperature and composition. FIG. 7 shows a high-level diagram of the airflow regulation system. Ambient air is drawn into the dual cartridge 401 through the vapor flow control valve 800. It is then drawn through the two chambers of the cartridge as shown and vapor flows through the main conduit 803 to the mouthpiece 101. Ambient air is drawn in through an ambient air conduit 801, controlled by the air flow control valve 802. The vapor flow control valve 800 and the air flow control valve 802 are controlled by the processor to ensure that the mixture of ambient air and vapor delivered at the mouthpiece is at the proper temperature for consumption-not so hot as to injure the lungs, but not so cold that the vapor condenses. The cooling and airflow regulation system enables independent control of the flow rate of both ambient air and vapor. The mouthpiece comprises a vortex generating profile that enables ambient air and vapor to be efficiently mixed and delivered to the user, as discussed below.

The vapor flow control valve and air flow control valve are preferably stepper valves comprising an endless screw mechanism, as discussed below. However, other valve designs may also be used for the present invention, as long as they provide sufficiently precise flow control.

User Interface

As discussed above, the user interface for an embodiment of the present invention comprises a touchscreen. The touchscreen is preferably a high-resolution TFT screen and capacitive touch sensor, but could be any other display and input device that provides a similar functionality. The graphical user interface (GUI) of the device preferably enables the user to manage dosing behavior of the device and to exercise precise control over their dosing experience, as well as to review statistics directly on the device.

Figure 8:
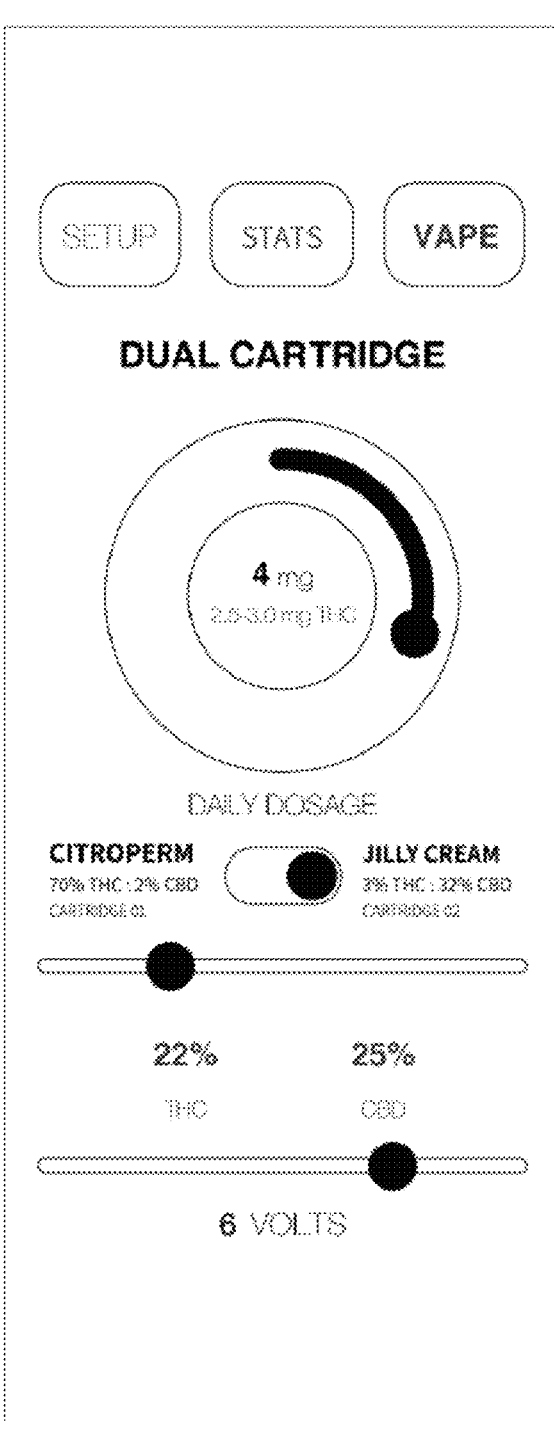
FIG. 8 shows a screenshot from the user interface of an embodiment of the present invention.

FIG. 8 shows a sample screenshot of an embodiment of the present invention. As can be seen, a round slider enables a user to set a daily dosage for at least one, possibly more than one, active compound in the cannabis. Two linear sliders enable the user to set a percentage of THC and a percentage of CBD in the vapor. The screen also displays the contents of each cartridge. In an embodiment, more than two linear sliders could be used, and the user could set the desired amounts or percentages for other substances in the vaporizable liquid, such as other cannabinoids or terpenes. In another embodiment, only one linear slider is used to set the THC: CBD ratio.

In an embodiment, a user could select a pre-programmed sequence of dosages or percentages for at least one active substance in the vapor. For example, a user could activate a program that gradually increases the percentage of THC in the vapor from 10% to 25% over a period of an hour, while decreasing the percentage of CBD in the vapor from 30% to 10%.

In an embodiment, the user could connect the vaporizer to a wearable fitness monitor or medical device to measure at least one physiological parameter. Such a wearable device could be a Fitbit, an Apple watch, or any other similar wearable device. The connection could happen by Wi-Fi, Bluetooth, or any other wireless connection protocol. A non-limiting list of the physiological parameters that could be relevant to the present invention is blood pressure, heart rate, heart rate variability, breathing rate, EKG, EEG, and so on. It is to be understood that any other physiological parameter that could be measured by a wearable device could be included in the present invention. In an embodiment, the user could set a pre-programmed sequence of dosages to depend on at least one physiological parameter. For example, the user could set a CBD percentage to be at 35% until the user's blood pressure goes down below a particular level, at which point the CBD percentage would decrease. Similarly, the user could set a vapor composition to contain a high amount of THC until a user's seizure activity stops as measured by an EEG, at which point the THC amount would decrease and the CBD amount would increase.

In an embodiment, the device could turn off altogether when a wearable device detects that the user's physiological parameter has reached a particular value. For example, the flow of vapor could stop once a user's blood pressure goes down below a particular level.

Figure 9:
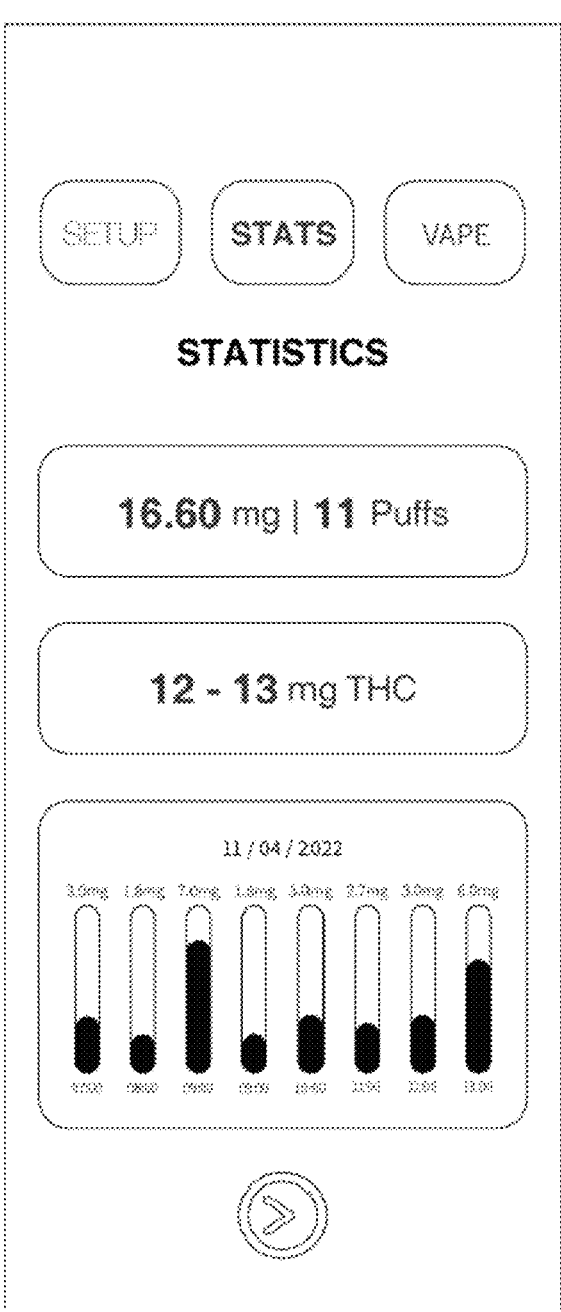
FIG. 9 shows another screenshot from the user interface of an embodiment of the present invention.

FIG. 9 shows a sample screenshot of the stats window of an embodiment of the present invention. In this embodiment, the screen displays how many puffs a user has taken, how many milligrams of vapor was inhaled, how much THC was inhaled, and what the user's usage history is. It is to be understood that in other embodiments, the stats window may also display the amount of CBD consumed, the amount of terpenes consumed (either collectively or individually), the time of day for each usage session, or any other information.

In an embodiment, a clinician could remotely set the relative amounts of the various active compounds in the vapor and the number of usage sessions and dosages that a user is supposed to consume. This is preferably done via a dashboard on the clinician's computer. FIG. 10 shows a sample screenshot from an embodiment of the dashboard. The dashboard also allows a clinician (or other user) to control the device remotely, to monitor a patient's vital signs, to see the dosage history, cartridge history, and other statistics about the patient's use of the device. It also allows the clinician to set a daily limit for a patient (which could be a limit on the number of usage sessions, the amount of an active compound consumed, the amount of vapor consumed, or any other parameter); in this embodiment, the device turns off when the daily limit is reached.

If a clinician changes the recommended dosage or other parameters, a user can see the changes on the touchscreen. In an embodiment, the user is able to accept or decline the dosage changes; in an alternate embodiment, the user is simply informed about the dosage changes without the ability to decline them.

In an embodiment, the dashboard is used by a recreational user of the device. In that embodiment, the user can load different profile presets to change the dose behavior. These presets can help users adjust the device's performance based on their specific needs, which can provide a more personalized and effective experience. In an embodiment, the dashboard can feature social interactions, and users can add their friends and then see their statistics and comment on them. Additionally, users can give direct feedback on the cartridges used in the device, providing an opportunity for learning and sharing among users. The dashboard preferably comprises security features such as encryption to protect patient data.

PID Controllers

In the preferred embodiment of the device of the present invention, each cartridge is heated independently by a heating unit controlled by a PID controller, which also controls the power and delivered dose for each cartridge. The PID-controlled heating modules don't only allow for real-time regulation of temperature, power, and delivered dose for each cartridge, but they are also controlled by a high-frequency PWM signal that can change its microsecond duty cycle to cater to evolving inhalation variables. These variables are specific to each user, and can change based on factors such as lung capacity, inhalation rate, and personal preference.

In an embodiment, the device uses two heating units, each independently controlled by a PID controller. (It is to be understood that any other number of heating units is also included in the present disclosure) The PID controller constantly monitors the temperature of each cartridge and adjusts the power output of the heating unit to maintain a constant temperature. In addition, the heating units are controlled by a high-frequency PWM (pulse-width modulation) signal. The PWM signal adjusts the power output of the heating unit by changing its microsecond duty cycle. By varying the duty cycle, the device can cater to evolving inhalation variables, such as changes in lung capacity, inhalation rate, and personal preference.

The device uses a sophisticated algorithm to calculate the optimal PWM duty cycle for each inhalation based on these variables. The algorithm takes into account factors such as the desired dose, the duration of the inhalation, and the user's lung capacity and inhalation rate to determine the ideal duty cycle. Overall, the combination of PID-controlled heating modules and high-frequency PWM signal allows the device to provide precise, real-time regulation of temperature, power, and delivered dose for each cartridge. This personalized dosing system provides a unique and innovative solution to the challenges of inhalation therapy.

The algorithm to calculate the optimal PWM (pulse width modulation) duty cycle takes into account various factors that can affect the inhalation experience for each user. These factors include the user's lung capacity, inhalation rate, and personal preference.

The algorithm uses a combination of machine learning techniques and real-time feedback from the pressure sensor to determine the optimal PWM duty cycle for each inhalation. The pressure sensor measures the pressure inside the cartridge during inhalation and feeds this information back to the algorithm in real-time. Based on this feedback, the algorithm adjusts the PWM duty cycle to ensure that the optimal amount of compound is delivered to the user with each inhalation. The algorithm continuously learns and adapts to each user's specific inhalation patterns, ensuring a consistent and optimal dose delivery with each use. Overall, this algorithm is a key component of the device, allowing for a personalized and precise inhalation experience for each user.

In an embodiment, the PID controller can be calibrated to a user's individual breathing parameters, such as inhalation rate and lung capacity. This initial calibration is important because it allows the PID controller to adjust its model in a personalized way for each user. By taking into account each user's unique breathing behaviors, such as inhalation rate and lung capacity, the device can deliver a more consistent and customized inhalation experience. In an embodiment, the PID controller can make real-time adjustments based on the user's inhalation variables and personal preferences, so that each puff is tailored to the user's specific needs.

In an embodiment, the PID controller offers various delivery methods that can be chosen based on the user's individual needs. For example, some delivery methods include constant voltage, inhalation dose, temperature control, and wattage control. Each delivery method can be adjusted in real time to ensure the user gets the most out of their inhalation experience.

a. Constant voltage: In this delivery method, the device maintains a constant voltage across the heating module during the inhalation process. This method is useful when the user prefers a consistent and predictable experience.

b. Inhalation dose: In this delivery method, the device delivers a pre-determined amount of compound with each inhalation. The PID controller adjusts the heating module's power and duration to ensure that the correct amount of compound is delivered. This method is useful when the user wants a specific dose of medication every time they use the device.

c. Temperature control: In this delivery method, the device maintains a constant temperature throughout the inhalation process. The PID controller adjusts the heating module's power to maintain the desired temperature. This method is useful when the user wants to control the temperature of the compound they inhale.

d. Wattage control: In this delivery method, the device maintains a constant wattage throughout the inhalation process. The PID controller adjusts the heating module's power and duration to maintain the desired wattage. This method is useful when the user wants a consistent and predictable experience, similar to constant voltage delivery.

Each of these delivery methods can be adjusted in real time to cater to the user's individual needs. For example, a user with a larger lung capacity may require more compound to be delivered with each inhalation, so the inhalation dose delivery method can be adjusted accordingly. Similarly, a user who prefers a specific temperature or wattage can use the temperature or wattage control delivery methods to customize their inhalation experience. Overall, the ability to choose from multiple delivery methods and adjust them in real time makes the device highly customizable and adaptable to each user's needs.

In an embodiment, the PID controller is tuned before use. This is performed by determining the characteristic curve of the heating element and determining the transfer function of the heating element using the temperature-time data of the characteristic curve. Then, the PID controller is tuned using a commonly used "PID Tuner" tool in Matlab or a similar software package, and the constants Kp, Ki and Kd are determined and the PID control function is obtained. This enables the PID controller to control the heating unit to achieve a desired temperature in as quick of a way as possible. Any commonly used PID tuning method may be used for practicing the present invention.

In an embodiment, the temperature set by the PID is further adjusted to account for vapor pressure. Boiling temperature is directly affected by the vapor pressure; therefore, if the temperature is set to the boiling point of a particular compound, it may not boil if the vapor pressure is different from what is expected. In an embodiment, a pressure sensor will adjust and correct the boiling temperature as a function of changes in vapor pressure. The amount of compound released (boiling point) is a function of resistor temperature and time period. Each resistor characteristic profile (resistor size and material) will allow the calculation of volume of vapor released during a specific time. The exact heating profile will be set by the use of gas chromatography and/or mass spectrometry and stored in memory.

Mouthpiece and Helicoidal Mixed Flow

In an aspect of the present invention, the mouthpiece of the vaporizer of the present invention provides a unique system of airflow channels that provide for a helical vortex of airflow. This is an advantage in that it provides for better mixing between the vapor coming from the cartridge and ambient air and cools down the vapor to an acceptable temperature for the user. The compound gas coming out of the cartridge is at a very high temperature; mixing it with ambient air lowers the temperature. If the temperature is lowered too much, however, the vapor will condense, which is undesirable. Since oil at different ranges of viscosity condenses at temperatures between 25° C.-29° C., the temperature of the gas mixture has to be maintained above 29° C. so that no oil droplets enter the user's mouth through the mouthpiece of the device. The average evaporation temperature of a vaporizable liquid is around 42° C. A comfortable inhalation temperature is around 30° C.

In the preferred embodiment of the present invention, strict regulation of the vapor flow and the ambient air flow ensures that the temperature of the mixture is kept consistent and constant. In an embodiment, the temperature of the mixture is kept at approximately 30° C.; in alternate embodiments, the temperature may be 31° C., or any other temperature as long as it is comfortable to inhale and does not cause condensation in the vapor. The temperature is kept constant by regulating the airflow and the flow of vapor in the device. In an embodiment of the present invention, a user may be able to set a desired temperature for the mixture.

Furthermore, the mouthpiece of the present invention accelerates the vapor flow and deliver more velocity to the lungs. This is especially relevant for vapor that contains terpenes. Some users desire more flavor in their vapor.

Terpenes provide the flavor, but they require lower heat for a longer time, which means the flow is slower. A user desiring higher flow in a conventional vaporizer would have to sacrifice flavor and terpene content. The present invention enables ambient air to be drawn into the mouthpiece at a high velocity, in such a way as to provide a helical vortex of air that mixes with the terpene-containing vapor and accelerates it out of the mouthpiece. This provides both flavor and flow.

Figure 11:
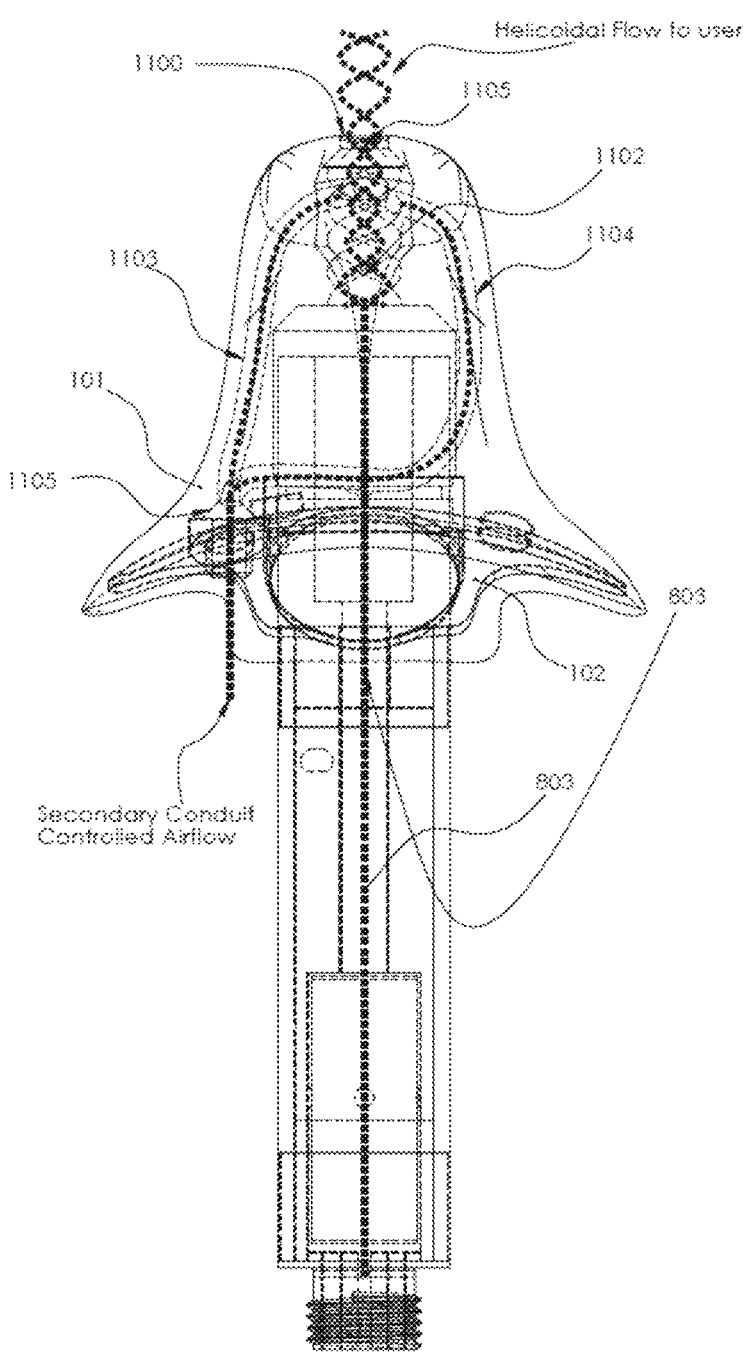
FIG. 11 shows a diagram of an embodiment of the mouthpiece showing the helicoidal flow of the exiting mixture of vapor and ambient air.

FIG. 11 shows a cross-sectional diagram of the mouthpiece 101 of the present invention, connected to a cartridge to show the airflow through the device. Vapor flows out of the cartridge through the main conduit 803. Ambient air flows into the mouthpiece through an ambient air conduit; the airflow is controlled by a stepper valve. As can be shown, the air is separated into two channels, a left channel 1103 and a right channel 1104. Those channels meet the inner helical section 1102 from opposite directions as shown, producing a helical vortex of airflow. The speed of the vortex draws in the vapor coming through the main conduit 803 and accelerates its flow through the mouthpiece, producing a helicoidal flow out of the opening 1100. This provides flavor and flow at the same time.

Figure 12:
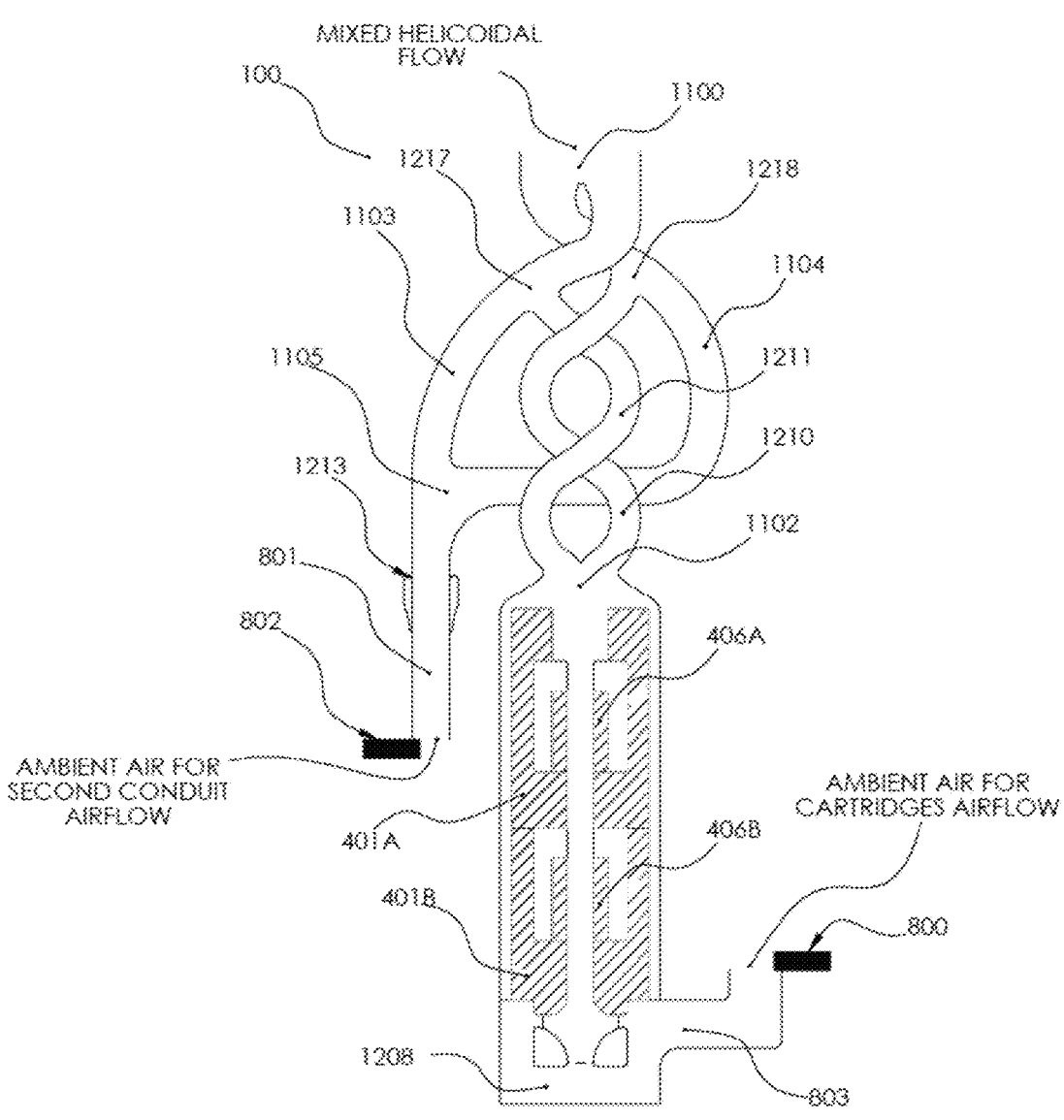
FIG. 12 shows a diagram of the air and vapor conduits through an embodiment of the mouthpiece showing the helicoidal conduits.

FIG. 12 shows a schematic view of the air conduits through the mouthpiece and cartridges to provide greater detail. Valves 800 and 802 control the flow of ambient air through the main conduit 803 and through the ambient air conduit 801, respectively. Ambient air is driven through the first cartridge 401B and second cartridge 401A by the power unit 1208; a first heating unit 406B and a second heating unit 406A vaporize the contents of each cartridge, respectively. When vapor is generated, it is driven into the start point 1102 for the two helicoidal conduits and then separated into two helicoidal conduits 1210 and 1211. The ambient air conduit 801 drives ambient air from the air flow control valve 802 to the nozzle fitting 1213. The airflow is separated at the airflow divergence point 1105 into a first secondary conduit 1103 and a second secondary conduit 1104. Those secondary conduits merge with the helicoidal conduits at points 1217 and 1218 to combine the vapor and the air. A helicoidal vortex is then created at the outlet 1100.

It is to be understood that while two helicoidal conduits are depicted, the present invention is not limited to the two helicoidal conduits, but may use three, four, or any other number of helicoidal conduits, and may also comprise three, four, or any other number of secondary conduits for ambient air.

The diameter of the ambient air conduit is preferably 3 mm, but could be any other diameter that provides adequate airflow and fits within the form factor. The diameter of the helical spiral is preferably 5 mm with 2 internal conduits of 2 mm inner diameter. In alternate embodiments, the spiral could be from 5 mm to 10 mm in diameter. In some embodiment of the invention, the mouthpiece could have more than two channels for the ambient air conduit, and the fact that only two channels are shown is not meant to be limiting.

Figure 13:
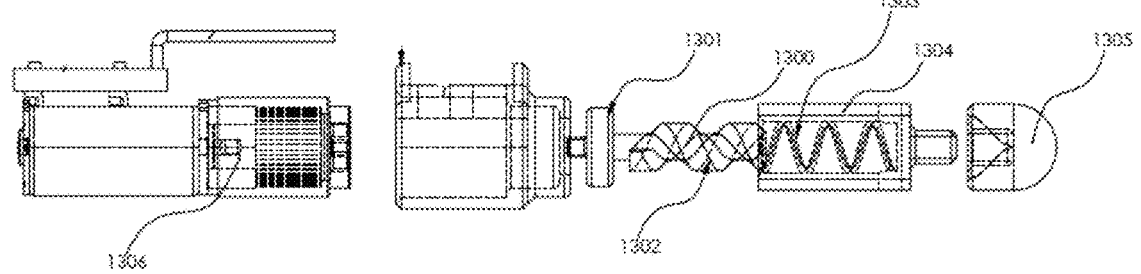
FIG. 13 shows a stepper valve used in an embodiment of the present invention.

The airflow through the ambient air conduit is preferably controlled by a stepper valve, though other devices that control airflow may also be used for the present invention. In an embodiment of the invention, a stepper valve as shown in FIG. 13 is used to control the airflow through the secondary conduit, and a second similar stepper valve is used to control the airflow through the cartridge. An exploded view of the stepper valve used for an embodiment of the present invention is shown in FIG. 13. An endless screw 1300 with thread 1302 is turned by a motor 1306. The motor 1306 is preferably a 4 mm stepper motor with a gearbox. The screw thread rotates to convert rotation into linear displacement to push the plug 1305 toward the valve seats to provide airflow or to close it off. The valve is held in place by a bracket to prevent the threaded stem from rotating in place. It is to be understood that any other device that controls airflow with a high degree of precision may also be used for the present invention.

Standard Cartridges

The device of the present invention can use any type of cartridge. In an embodiment of the present invention, the device uses standard 510 cartridges. This enables a broader selection of liquids and better availability.

Figure 14:
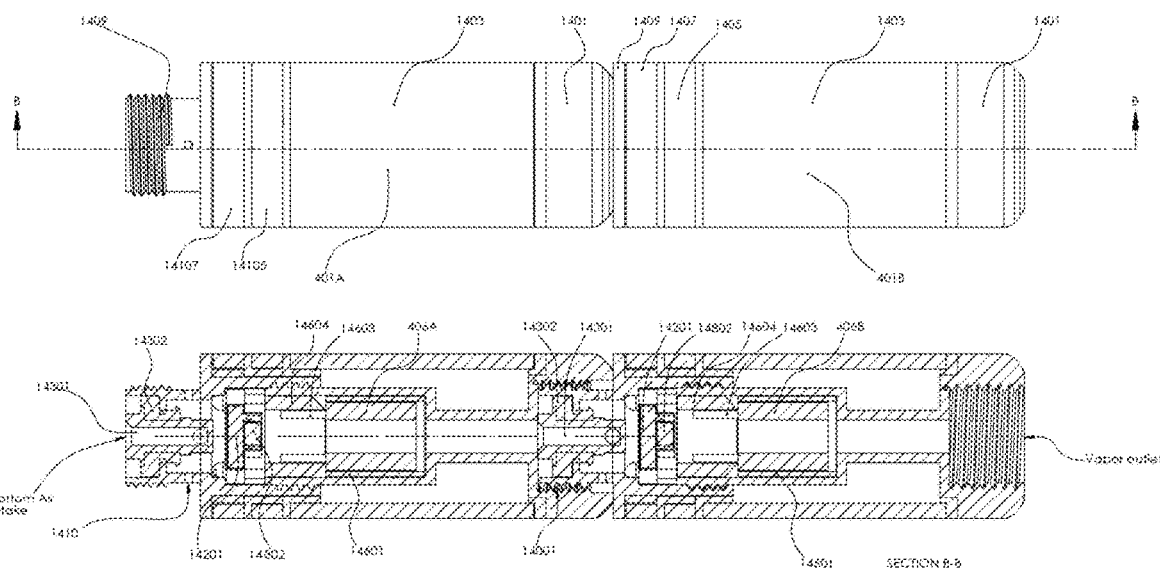
FIG. 14 shows a cross-sectional view of a dual cartridge of an embodiment of the present invention.

In an embodiment, dual or triple cartridges are used. In an embodiment, such cartridges still fit in the same space as a standard 510 cartridge. In this embodiment, two (or more) cartridges can be screwed together to form a unit with a form factor similar to a standard 510 cartridge. FIG. 14 shows a cross-sectional view of a dual cartridge of an aspect of the present invention. As can be seen, both the first cartridge 401B and the second cartridge 401A are identical in form factor (though this is not required to practice the present invention). They both comprise a glass container 1403 and a stainless steel atomizing tube 1401. The atomizing tube 1401 comprises a threaded hole for another cartridge to be screwed into it with standard 510 thread 1409 (a standard 510 cartridge thread, M6.8×0.5 mm). A positive contact ring 14105 is used for the secondary cartridge power supply, and a signal contact ring 14107 is used for a one-wire EEPROM inside the cartridge.

As can be seen on the cross-sectional view, the two cartridges screw together and the main conduit forms a continuous channel through the two cartridges. Each cartridge comprises a heating unit 406A and 406B. In an embodiment, this is a ceramic heater with a stainless steel resistor for 3-5V voltage. A cotton liner 14601 and a rubber gasket 14604 are used to keep the ceramic heater in place and reduce leaks. Coil contact wires 14603 are used to connect the heater to the controller. A one-wire EEPROM 14802 is used to connect to the heating unit. Ambient air comes through from the bottom air intake and the lateral air intake and goes through the main conduit from the primary cartridge to the secondary cartridge to the vapor outlet, as shown. The lateral air intake is needed because the 510 cartridges have an internal atomizing tube with a 3 mm diameter flow; to feed this conduit properly, several air intakes are needed. Because the bottom of the cartridge has a gasket and a positive contact, a 3 mm intake hole is not possible; furthermore, the sides of the base need the threads to screw onto the power unit. Therefore, side holes are added to increase airflow in the cartridge. In an embodiment, 4 side holes of 0.5 mm diameter are used. It is to be understood that any other number and diameter of side holes may also be used for the present invention, as long as enough airflow is provided.

As can be seen in the Figure, each cartridge contains a vaporizable liquid substance. The two cartridges can contain the same liquid or different liquids. In an embodiment, one cartridge can contain a liquid that contains mostly CBD, while the other cartridge can contain a liquid that contains mostly THC. In another embodiment, one cartridge can contain a liquid that is high in a particular cannabinoid or terpene, while the other cartridge can contain a liquid that is high in a different cannabinoid or terpene.

While the above-described figures show certain dimensions, it is to be understood that the dimensions apply only to this particular embodiment of the invention and that the present invention is not limited by those particular dimensions. Furthermore, the invention encompasses reasonable equivalents to all the above-described components or elements as is evident to a person of reasonable skill in the art.

The invention claimed is:

1. A method of providing an inhalable substance to a user, comprising:

providing a vaporizer comprising at least one cartridge and a heating unit, wherein the vaporizer further comprises at least one processor, a memory, a controller, and an input device;

providing a liquid substance in the at least one cartridge, wherein the liquid substance comprises at least two vaporizable compounds, a first compound and a second compound, wherein the first compound has a different boiling point from the second compound;

using the input device to set a desired first vapor composition, wherein the first vapor composition comprises a predetermined percentage of the first compound and a predetermined percentage of the second compound;

using the processor to determine a first temperature, wherein the first temperature is a temperature to which the liquid substance needs to be heated to result in the first vapor composition;

using the heating unit to heat the liquid substance to the first temperature to result in a first vapor having the first vapor composition;

delivering the first vapor to a user;

using the processor to determine a second temperature, wherein the second temperature is a temperature to which the liquid substance needs to be heated to result in a second vapor composition, wherein the second vapor composition is different from the first vapor composition in at least one of the following: percentage of the first compound, percentage of the second compound;

changing the temperature of the heating unit to heat the liquid substance to a second temperature to result in a second vapor having the second vapor composition;

delivering the second vapor to a user.

2. The method of claim 1, further comprising:

prior to delivering the first vapor to a user, mixing a predetermined amount of ambient air with the first vapor to obtain a gas mixture at approximately 30° C.;

prior to delivering the second vapor to a user, mixing a predetermined amount of ambient air with the second vapor to obtain a gas mixture at approximately 30° C.

3. The method of claim 2, wherein the step of mixing a predetermined amount of ambient air with the first vapor to obtain a gas mixture at approximately 30° C. comprises:

calibrating the vaporizer by at least one of the following: measuring a user's inhalation volume, calculating a user's inhalation volume from the user's biometric parameters;

calculating a flow rate of ambient air and a flow rate of first vapor required to obtain a gas mixture at approximately 30° C.;

controlling the flow rate of ambient air and the flow rate of first vapor in order to obtain the gas mixture at approximately 30° C.

4. The method of claim 3, wherein the step of mixing a predetermined amount of ambient air with the first vapor is performed by directing the ambient air along a helical path to create a vortex that accelerates the first vapor.

5. The method of claim 1, further comprising:

measuring at least one physiological parameter of the user continuously throughout a use session;

wherein the step of changing the temperature of the heating unit is performed after at least one physiological parameter reaches a predetermined value.

6. The method of claim 5, further comprising:

stopping the provision of vapor to the user after at least one physiological parameter reaches a predetermined value.

7. The method of claim 1, wherein the first temperature is the boiling point of the first compound.

8. The method of claim 7, wherein the first temperature is at a boiling point of the first compound and wherein the second temperature is the boiling point of the second compound, and wherein the step of using the heating unit to heat the liquid substance to a first temperature further comprises:

measuring a vapor pressure of the liquid substance;

adjusting the first temperature of the heating unit depending on vapor pressure in order to maintain the temperature at the boiling point of the first compound;

and wherein the step of using the heating unit to heat the liquid substance to a second temperature further comprises:

measuring a vapor pressure of the liquid substance;

adjusting the temperature of the heating unit depending on vapor pressure in order to maintain the second temperature at the boiling point of the second compound.

9. The method of claim 1, wherein the vaporizer comprises a second cartridge and a second heating unit, further comprising:

providing a second liquid substance in the second cartridge, wherein the second liquid substance contains the first compound and the second compound;

using the second heating unit to heat the second liquid substance to a third temperature to result in a third vapor having a third vapor composition, wherein the third vapor composition comprises a predetermined percentage of the first compound and a predetermined percentage of the second compound;

changing the temperature of the second heating unit to heat the second liquid substance to a fourth temperature to result in a fourth vapor having a fourth vapor composition, wherein the fourth vapor composition is different from the third vapor composition in at least one of the following: percentage of the first compound, percentage of the second compound;

performing at least one of the following actions to obtain a first mixed vapor:

mixing the first vapor and the third vapor;

mixing the first vapor and the fourth vapor;

mixing the second vapor and the third vapor;

mixing the second vapor and the fourth vapor;

delivering the first mixed vapor to the user;

performing at least one of the following actions to obtain a second mixed vapor, wherein the second mixed vapor has a different vapor composition from the first mixed vapor:

mixing the first vapor and the third vapor;

mixing the first vapor and the fourth vapor;

mixing the second vapor and the third vapor;

mixing the second vapor and the fourth vapor;

delivering the second mixed vapor to the user.

10. The method of claim 1, wherein the liquid substance further comprises a third compound, wherein the third compound has a different boiling point from either the first compound or the third compound, wherein the first vapor composition comprises a predetermined percentage of the third compound and wherein the second vapor composition is different from the first vapor composition in at least one of the following: percentage of the first compound, percentage of the second compound, percentage of the third compound.

11. The method of claim 1, wherein the step of changing the temperature of the heating unit is performed gradually over a predetermined period of time.

12. The method of claim 1, further comprising:
calibrating the vaporizer to determine at least one correlation between a temperature of the heating unit and a vapor composition by performing one of the following steps: gas chromatography, mass spectrometry;
storing the at least one correlation in memory.

13. A vaporizer device for vaporizing a substance, comprising:
a cartridge containing a liquid substance to be vaporized, the liquid substance comprising at least two compounds, a first compound and a second compound, wherein the first compound has a different boiling point from the second compound;
a heating module connected to the cartridge, wherein the heating module heats the liquid substance;
a pressure sensor to determine vapor pressure inside the cartridge;
a user interface;
a display;
a processor connected to the pressure sensor and the heating module, wherein the processor is configured to:
activate the heating module to heat the liquid substance to a first temperature to produce a first vapor, wherein the first vapor has a first vapor composition, comprising a predetermined percentage of the first compound and a predetermined percentage of the second compound;
change the temperature of the heating module to heat the liquid substance to a second temperature to produce a second vapor, wherein the second vapor has a second vapor composition comprising a predetermined percentage of the first compound and a predetermined percentage of the second compound, wherein the second vapor composition is different from the first vapor composition;
a mouthpiece to deliver vapor to a user;
a vapor flow control valve to regulate the flow of vapor to the mouthpiece;
an air flow control valve to regulate the flow of ambient air to the mouthpiece;
wherein the controller is further configured to:
regulate the vapor flow control valve and the air flow control valve to ensure that the mixture of vapor and ambient air delivered to the mouthpiece is at a temperature of approximately 30° C.

14. The vaporizer of claim 13, further comprising:
an ambient air conduit connected to the air flow control valve, said ambient air conduit comprising a first channel and a second channel;
wherein the mouthpiece comprises a first helical conduit and a second helical conduit, wherein the first helical conduit is connected to the first channel, wherein the second helical conduit is connected to the second channel, wherein both helical conduits are connected to an opening in the mouthpiece for delivering vapor to the user;
wherein the first helical conduit and the second helical conduit are also connected to a vapor conduit conducting vapor from the cartridge;
wherein the first helical conduit and the second helical conduit are configured in such a way as to impart a rotational velocity to a mixture of ambient air and vapor exiting the mouthpiece and to produce a vortex in the mixture of ambient air and vapor.

15. The vaporizer of claim 14, wherein the cartridge and the second cartridge are 510 threaded cartridges.

16. The vaporizer of claim 13, further comprising:
a second cartridge containing a second liquid substance to be vaporized, the second liquid substance comprising at least the first compound and the second compound;
a second heating module connected to the second cartridge, wherein the second heating module heats the second liquid substance;
a second pressure sensor to determine vapor pressure inside the second cartridge;
wherein the controller is further configured to:
activate the second heating module to heat the second liquid substance to a third temperature to produce a third vapor, wherein the third vapor has a third vapor composition, comprising a predetermined percentage of the first compound and a predetermined percentage of the second compound;
change the temperature of the second heating module to heat the second liquid substance to a fourth temperature to produce a fourth vapor, wherein the fourth vapor has a fourth vapor composition comprising a predetermined percentage of the first compound and a predetermined percentage of the second compound, wherein the fourth vapor composition is different from the third vapor composition;
a second vapor flow control valve to regulate the flow of third vapor to the mouthpiece;
wherein the mouthpiece is configured to produce and deliver at least one of the following mixtures to the user:
a mixture of ambient air, first vapor, and third vapor;
a mixture of ambient air, second vapor, and third vapor;
a mixture of ambient air, first vapor, and fourth vapor;
a mixture of ambient air, second vapor, and fourth vapor;
wherein the controller is further configured to regulate the second vapor flow control valve so that the at least one mixture is at approximately 30° C.

17. The vaporizer of claim 13, further comprising:
a communication module for communicating wirelessly with at least one wearable device for measuring at least one physiological parameter;
wherein the communication module is connected to the controller;
wherein the controller is configured to perform one of the following actions if the at least one wearable device communicates that a predetermined value of the at least one physiological parameter is reached:
change the temperature of the heating module;
turn off the heating module.

18. The vaporizer of claim 13, further comprising:
a communication module for communicating wirelessly with a computing device;
wherein the communication module is connected to the controller;
wherein the controller is configured to perform one of the following actions if the computing device sends a signal to the communication module:
change the temperature of the heating module;
turn off the heating module.

19. The vaporizer of claim 13, wherein the liquid substance comprises at least one third compound, said third compound having a boiling point that is different from the boiling point of the first compound and the boiling point of the second compound.

20. The vaporizer of claim 13, further comprising:

a user interface comprising a display and an input device for entering data, wherein the input device enables a user to enter a desired percentage of at least one of the first compound and the second compound;

wherein the controller is configured to adjust the temperature of the heating module and the second heating module in such a way that the mixture delivered to the user comprises the desired percentage entered by the user.

* * * * *